US00PP17858P2

(12) United States Plant Patent
Herdegen

(10) Patent No.: US PP17,858 P2
(45) Date of Patent: Jul. 10, 2007

(54) ***ERYSIMUM* PLANT NAMED 'LEMON ZEST'**

(50) Latin Name: *Erysimum hybrida*
Varietal Denomination: Lemon Zest

(75) Inventor: Susanne Herdegen, Undenheim (DE)

(73) Assignee: Innova Plant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/299,961

(22) Filed: Dec. 12, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Erysimum* plant named 'Lemon Zest', characterized by its compact, upright and outwardly spreading plant habit; freely branching growth habit; early flowering habit; and numerous light yellow-colored flowers.

1 Drawing Sheet

Botanical designation: *Erysimum hybrida.*
Cultivar denomination: 'Lemon Zest'.

BACKGROUND OF THE INVENTION

The present Invention relates to a new and distinct cultivar of *Erysimum* plant, botanically known as *Erysimum hybrida,* and hereinafter referred to by the name 'Lemon Zest'.

The new *Erysimum* is a product of a planned breeding program conducted by the Inventor in Gensingen, Germany. The objective of the breeding program was to create new compact pot-type *Erysimum* cultivars with early and freely flowering habit.

The new *Erysimum* originated from a cross-pollination made by the Inventor in 1999 of the *Erysimum hybrida* cultivar Sprite, not patented, as the female, or seed, parent with an unnamed selection of *Erysimum hybrida,* not patented, as the male, or pollen, parent. The new *Erysimum* was discovered and selected by the Inventor as a flowering plant within the resultant progeny of the stated cross-pollination in a controlled environment in Gensingen, Germany in 1999.

Asexual reproduction of the new *Erysimum* by terminal cuttings in Gensingen, Germany since 1999, has shown that the unique features of this new *Erysimum* are stable and reproduced true to type in successive generations of asexual reproduction.

SUMMARY OF THE INVENTION

The following traits have been repeatedly observed and are determined to be the unique characteristics of 'Lemon Zest'. These characteristics in combination distinguish 'Lemon Zest' as a new and distinct cultivar:

1. Compact, upright and outwardly spreading plant habit.
2. Freely branching growth habit.
3. Early flowering habit.
4. Numerous light yellow-colored flowers.

Plants of the new *Erysimum* differ from plants of the female parent, the cultivar Sprite, in the following characteristics:

1. Plants of the new *Erysimum* are more compact than plants of the cultivar Sprite.
2. Plants of the new *Erysimum* are more freely branching than plants of the cultivar Sprite.
3. Flowers of plants of the new *Erysimum* have broader and more intensely-colored petals than flowers of plants of the cultivar Sprite.

Plants of the new *Erysimum* differ from plants of the male parent selection primarily in the following characteristics:

1. Plants of the new *Erysimum* are more compact than plants of the male parent selection.
2. Plants of the new *Erysimum* are more freely branching than plants of the male parent selection.

Plants of the new *Erysimum* can be compared to plants of the *Erysimum* cultivar Orange Flame, not patented. In side-by-side comparisons conducted in Gensingen, Germany, plants of the new *Erysimum* differed primarily from plants of the cultivar Orange Flame in flower color as plants of the cultivar Orange Flame have orange-colored flowers.

BRIEF DESCRIPTION OF THE PHOTOGRAPHS

The accompanying colored photographs illustrate the overall appearance of the new *Erysimum,* showing the colors as true as it is reasonably possible to obtain in colored reproductions of this type. Colors in the photographs may differ slightly from the color values cited in the detailed botanical description which accurately describe the colors of the new *Erysimum.*

The photograph at the bottom of the sheet comprises a side perspective view of a typical plant of 'Lemon Zest' grown in a container.

The photograph at the top of the sheet is a close-up view of typical flowers of 'Lemon Zest'.

DETAILED BOTANICAL DESCRIPTION

The new *Erysimum* has not been observed under all possible environmental conditions. The phenotype may vary somewhat with variations in environment such as temperature and light intensity, without, however, any variance in genotype.

The aforementioned photographs, following observations and measurements describe plants grown in Bonsall, Calif. in an outdoor nursery during the spring and early summer under commercial production practices. Plants were about 24 weeks from planting rooted young plants when the photographs and description were taken. During the production of the plants, day temperatures ranged from 10° C. to 32° C. and night temperatures ranged from 4° C. to 21° C. In the following description, color references are made to The Royal Horticultural Society Colour Chart, 1995 Edition, except where general terms of ordinary dictionary significance are used.

Botanical classification: *Erysimum hybrida* cultivar Lemon Zest.

Parentage:

*Female, or seed, parent.*—*Erysimum hybrida* cultivar Sprite, not patented.

*Male, or pollen, parent.*—Unnamed selection of *Erysimum hybrida,* not patented.

Propagation:

*Type.*—By cuttings.

*Time to initiate roots, summer.*—About 14 days at 20° C.

*Time to initiate roots, winter.*—About 18 days at 20° C.

*Time to produce a rooted cutting.*—About 20 days at 20° C.

*Root description.*—Fine; white in color.

*Rooting habit.*—Freely branching.

Plant description:

*Plant form.*—Compact, upright to somewhat outwardly spreading; perennial in mild climates.

*Growth habit.*—Moderately vigorous. Freely branching, about eight primary branches with secondary branches potentially developing at every node.

*Plant height.*—About 32 cm.

*Plant width* (*spread*).—About 29 cm.

*Lateral branches.*—Length: About 14 cm. Diameter: About 3 mm. Internode length: About 4 mm. Strength: Strong. Texture: Smooth, glabrous. Color, immature: 145C. Color, mature: 199B.

*Foliage description.*—Arrangement: Alternate, simple. Length: About 3.5 cm. Width: About 1.1 cm. Shape: Oblanceolate. Apex: Acute. Base: Attenuate. Margin: Mostly entire with four shallow points. Texture, upper and lower surfaces: Smooth, glabrous. Venation pattern: Pinnate; arcuate. Color: Developing leaves, upper and lower surfaces: 147B. Fully expanded leaves, upper and lower surfaces: 147B; venation, 147B. Petiole length: About 3.5 cm. Petiole diameter: About 1 mm. Petiole texture, upper and lower surfaces: Smooth, glabrous. Petiole color, upper and lower surfaces: 146C.

Flower description:

*Flower type/habit.*—Single rounded flowers arranged in long terminal racemes; flowers face upright and outward. Freely flowering habit with about 50 flowering stems each with about 32 flower buds and flowers. Flowers not fragrant.

*Natural flowering season.*—Continuously flowering from March through May in Southern California. Flowers not persistent.

*Postproduction longevity.*—Flowers last about five to seven days on the plant.

*Inflorescence height.*—About 30 cm.

*Inflorescence diameter.*—About 4 cm.

*Flower buds.*—Height: About 1.2 cm. Diameter: About 4 mm. Shape: Oblong. Color: 2B.

*Flowers.*—Diameter: About 1.5 cm. Depth: About 1.6 cm.

*Petals.*—Quantity per flower: Typically four in a single whorl. Length: About 1.6 cmm. Lobe width: About 7 mm. Lobe shape: Spatulate. Apex: Rounded to very slightly emarginate. Base: Attenuate. Margin: Entire. Texture, upper and lower surfaces: Smooth, glabrous. Color: Developing petals, upper and lower surfaces: 2B. Fully expanded petals, upper surface: 2A to 2B; color becoming closer to 2C with development. Fully expanded petals, lower surface: 2B to 2C.

*Sepals.*—Quantity per flower: Typically four in a single whorl. Length: About 1 cm. Width: About 2 mm. Shape: Lanceolate. Apex: Acute. Base: Truncate. Texture, upper and lower surfaces: Smooth, glabrous. Color, upper surface: 145C. Color, lower surface: 145A.

*Peduncles.*—Length: About 2.5 cm. Diameter: About 2 mm. Aspect: Upright to curling with development. Strength: Moderately strong. Texture: Smooth, glabrous. Color: 147B.

*Pedicels.*—Length: About 4 mm. Diameter: About 1 mm. Aspect: About 45° from peduncle axis. Strength: Strong. Texture: Smooth, glabrous. Color: 144B.

*Reproductive organs.*—Stamens: Quantity per flower: Typically six. Anther shape: Oblong. Anther size: Less than 1 mm by about 3 mm. Anther color: 150B. Pollen amount: Scarce. Pollen color: 160B. Pistils: Quantity per flower: Typically one. Pistil length: About 1.8 cm. Stigma shape: Rounded. Stigma color: 145A. Style length: About 1.6 cm. Style color: 144B. Ovary color: 144B.

*Seed/fruit.*—Seed and fruit development have not been observed.

Disease/pest resistance: Plants of the new *Erysimum* have not been observed to be resistant to pathogens and pests common to *Erysimum.*

Temperature tolerance: Plants of the new *Erysimum* have been observed to tolerate high temperatures of 40° C. and are hardy to USDA Zone 8.

It is claimed:

1. A new and distinct cultivar of *Erysimum* plant named 'Lemon Zest', as illustrated and described.

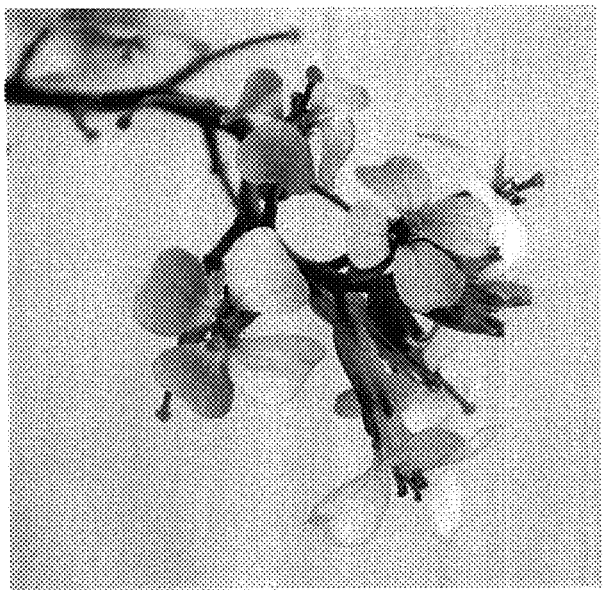
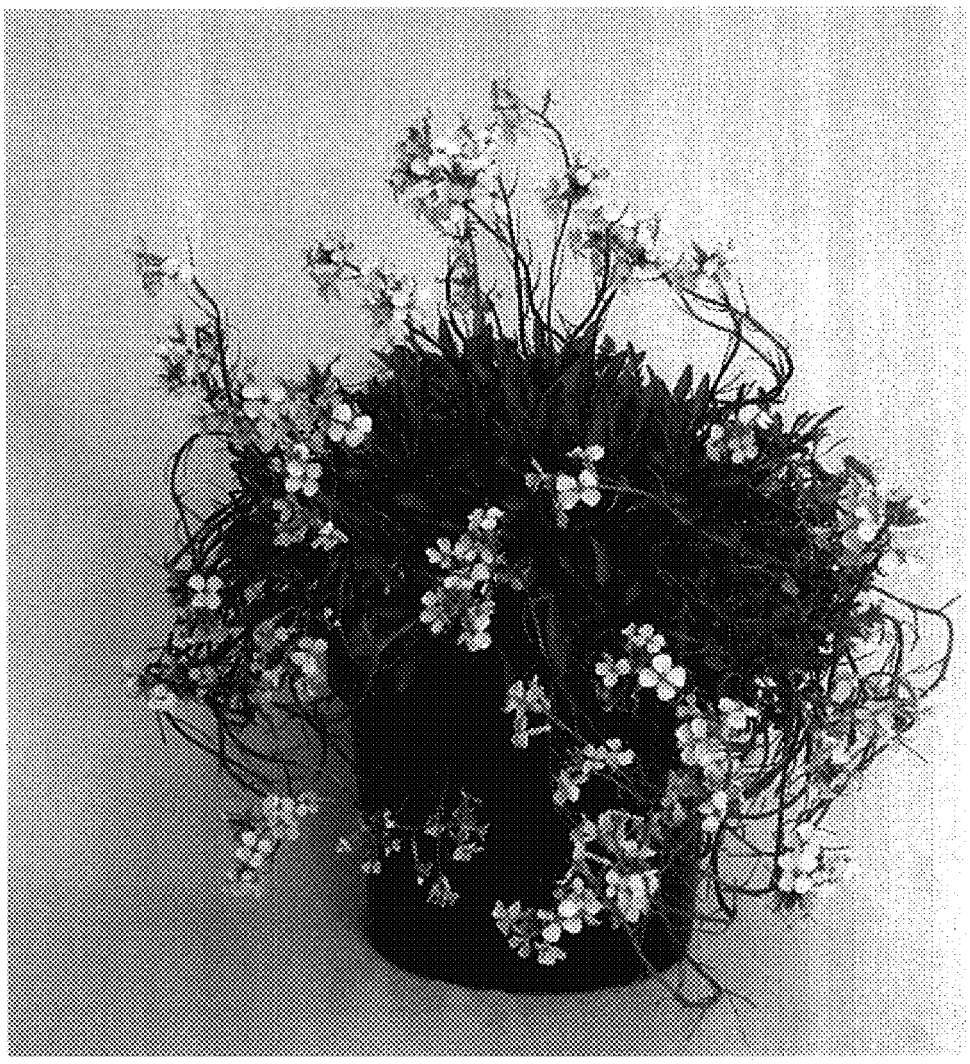

* * * * *